(12) United States Patent
Nose et al.

(10) Patent No.: US 8,883,972 B2
(45) Date of Patent: Nov. 11, 2014

(54) HIGH SPECIFICITY MONOCLONAL ANTIBODY AGAINST A PROTEIN OR A POLYPEPTIDE HAVING OXIDATIVE MODIFICATION

(75) Inventors: Hiroshi Nose, Hyogo (JP); Tomoyo Hashiguchi, Hyogo (JP); Masaya Ono, Tokyo (JP); Tesshi Yamada, Tokyo (JP); Setsuo Hirohashi, Tokyo (JP)

(73) Assignees: Transgenic Inc., Kumamoto (JP); President, National Cancer Center, Tokyo (JP)

( * ) Notice: Subject to any disclaimer, the term of this patent is extended or adjusted under 35 U.S.C. 154(b) by 403 days.

(21) Appl. No.: 12/379,084

(22) Filed: Feb. 12, 2009

(65) Prior Publication Data

US 2010/0092994 A1    Apr. 15, 2010

(30) Foreign Application Priority Data

Oct. 14, 2008  (JP) ................. 2008-264742
Dec. 25, 2008  (JP) ................. 2008-330745

(51) Int. Cl.
*C07K 16/00* (2006.01)
*G01N 33/574* (2006.01)
*C07K 16/36* (2006.01)
*C07K 16/30* (2006.01)
*C07K 16/44* (2006.01)

(52) U.S. Cl.
CPC .......... *C07K 16/44* (2013.01); *G01N 33/57438* (2013.01); *C07K 16/36* (2013.01); *C07K 16/303* (2013.01)
USPC ...................... 530/387.1; 435/326

(58) Field of Classification Search
None
See application file for complete search history.

(56) References Cited

U.S. PATENT DOCUMENTS

2004/0023854 A1 *   2/2004   Cooper et al. .................. 514/8

FOREIGN PATENT DOCUMENTS

JP     2006-177811 A      7/2006

OTHER PUBLICATIONS

Molina et al, Molecular Cellular Proteomics, 4:637-650, 2005.*
Kageyama et al, FASEB Journal express article, 10.1096/Fj.03-1233fje; published online Apr. 14, 2004.*
Data sheet of fibrinogen gene/protein in National Library of Medline 2010.*
S. M. Boekholdt et al., "Fibrinogen plasma levels modify the association between the factor XIII Val34Leu variant and risk of coronary artery disease: the EPIC-Norfolk prospective population study", Journal of Thrombosis and Haemostasis, vol. 4, pp. 2204-2209, 2006.
Campbell R. Sheen et al., "Fibrinogen Montreal: A novel missense mutation (Aα D496N) associated with hypofibrinogenaemia", Thromb Haemost, vol. 96, No. 2, pp. 231-232, 2006.
Jaap Koopman et al., "Fibrinogen Marburg: A Homozygous Case of Dysfibrinogenemia, Lacking Amino Acids Aα 461-610 (Lys 461 AAA→ Stop TAA)", Blood, vol. 80, No. 8, pp. 1972-1979, Oct. 15, 1992.
Denise A. Chan et al., "Role of Prolyl Hydroxylation in Oncogenically Stabilized Hypoxia-inducible Factor-1α", The Journal of biological chemistry, 2002, vol. 277, No. 42, p. 40112-40117.
Agnes H. Henschen-Edman, "Fibrinogen Non-Inherited Heterogeneity and Its Relationship to Function in Health and Disease", Annals of the New York Academy of Sciences, 2001, vol. 936, p. 580-593.

* cited by examiner

*Primary Examiner* — Lei Yao

(74) *Attorney, Agent, or Firm* — Birch, Stewart, Kolasch & Birch, LLP

(57) ABSTRACT

The present invention provides an antibody, which reacts with a FGA or FGA partial peptide in which a part of prolines in the molecule thereof are hydroxylated, and which does not react with an unmodified FGA or FGA partial peptide.

22 Claims, 7 Drawing Sheets
(4 of 7 Drawing Sheet(s) Filed in Color)

a b

■ 565HP-α fibrinogen
■ α fibrinogen

CC=0.22

SEQUENCE LISTING

```
<160> NUMBER OF SEQ ID NOS: 7

<210> SEQ ID NO 1
<211> LENGTH: 20
<212> TYPE: PRT
<213> ORGANISM: Homo sapiens

<400> SEQUENCE: 1

Thr Phe Pro Gly Phe Phe Ser Pro Met Leu Gly Glu Phe Val Ser Glu
1               5                   10                  15

Thr Glu Ser Arg
            20

<210> SEQ ID NO 2
<211> LENGTH: 15
<212> TYPE: PRT
<213> ORGANISM: Homo sapiens

<400> SEQUENCE: 2

Glu Ser Ser Ser His His Pro Gly Ile Ala Glu Phe Pro Ser Arg
1               5                   10                  15

<210> SEQ ID NO 3
<211> LENGTH: 20
<212> TYPE: PRT
<213> ORGANISM: Homo sapiens
<220> FEATURE:
<221> NAME/KEY: misc_feature
```

```
<222> LOCATION: (3)..(3)
<223> OTHER INFORMATION: Hydroxylated proline

<400> SEQUENCE: 3

Thr Phe Pro Gly Phe Phe Ser Pro Met Leu Gly Glu Phe Val Ser Glu
1               5                   10                  15

Thr Glu Ser Arg
            20

<210> SEQ ID NO 4
<211> LENGTH: 15
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Hydroxylated proline

<400> SEQUENCE: 4

Glu Ser Ser Ser His His Pro Gly Ile Ala Glu Phe Pro Ser Arg
1               5                   10                  15

<210> SEQ ID NO 5
<211> LENGTH: 644
<212> TYPE: PRT
<213> ORGANISM: Homo sapiens

<400> SEQUENCE: 5

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
                20                  25                  30

Gly Val Arg Gly Pro Arg Val Val Glu Arg His Gln Ser Ala Cys Lys
            35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240
```

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 6

-continued

```
<211> LENGTH: 866
<212> TYPE: PRT
<213> ORGANISM: Homo sapiens

<400> SEQUENCE: 6

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
```

```
              385                 390                 395                 400
         Gly Asn Ala Arg Pro Asn Asn Pro Asp Trp Gly Thr Phe Glu Glu Val
                             405                 410                 415

Ser Gly Asn Val Ser Pro Gly Thr Arg Arg Glu Tyr His Thr Glu Lys
                             420                 425                 430

Leu Val Thr Ser Lys Gly Asp Lys Glu Leu Arg Thr Gly Lys Glu Lys
                             435                 440                 445

Val Thr Ser Gly Ser Thr Thr Thr Thr Arg Arg Ser Cys Ser Lys Thr
                             450                 455                 460

Val Thr Lys Thr Val Ile Gly Pro Asp Gly His Lys Glu Val Thr Lys
         465                 470                 475                 480

Glu Val Val Thr Ser Glu Asp Gly Ser Asp Cys Pro Glu Ala Met Asp
                             485                 490                 495

Leu Gly Thr Leu Ser Gly Ile Gly Thr Leu Asp Gly Phe Arg His Arg
                             500                 505                 510

His Pro Asp Glu Ala Ala Phe Phe Asp Thr Ala Ser Thr Gly Lys Thr
                             515                 520                 525

Phe Pro Gly Phe Phe Ser Pro Met Leu Gly Glu Phe Val Ser Glu Thr
                             530                 535                 540

Glu Ser Arg Gly Ser Glu Ser Gly Ile Phe Thr Asn Thr Lys Glu Ser
         545                 550                 555                 560

Ser Ser His His Pro Gly Ile Ala Glu Phe Pro Ser Arg Gly Lys Ser
                             565                 570                 575

Ser Ser Tyr Ser Lys Gln Phe Thr Ser Ser Thr Ser Tyr Asn Arg Gly
                             580                 585                 590

Asp Ser Thr Phe Glu Ser Lys Ser Tyr Lys Met Ala Asp Glu Ala Gly
                             595                 600                 605

Ser Glu Ala Asp His Glu Gly Thr His Ser Thr Lys Arg Gly His Ala
                             610                 615                 620

Lys Ser Arg Pro Val Arg Asp Cys Asp Asp Val Leu Gln Thr His Pro
         625                 630                 635                 640

Ser Gly Thr Gln Ser Gly Ile Phe Asn Ile Lys Leu Pro Gly Ser Ser
                             645                 650                 655

Lys Ile Phe Ser Val Tyr Cys Asp Gln Glu Thr Ser Leu Gly Gly Trp
                             660                 665                 670

Leu Leu Ile Gln Gln Arg Met Asp Gly Ser Leu Asn Phe Asn Arg Thr
                             675                 680                 685

Trp Gln Asp Tyr Lys Arg Gly Phe Gly Ser Leu Asn Asp Glu Gly Glu
                             690                 695                 700

Gly Glu Phe Trp Leu Gly Asn Asp Tyr Leu His Leu Leu Thr Gln Arg
         705                 710                 715                 720

Gly Ser Val Leu Arg Val Glu Leu Glu Asp Trp Ala Gly Asn Glu Ala
                             725                 730                 735

Tyr Ala Glu Tyr His Phe Arg Val Gly Ser Glu Ala Glu Gly Tyr Ala
                             740                 745                 750

Leu Gln Val Ser Ser Tyr Glu Gly Thr Ala Gly Asp Ala Leu Ile Glu
                             755                 760                 765

Gly Ser Val Glu Glu Gly Ala Glu Tyr Thr Ser His Asn Asn Met Gln
                             770                 775                 780

Phe Ser Thr Phe Asp Arg Asp Ala Asp Gln Trp Glu Glu Asn Cys Ala
         785                 790                 795                 800

Glu Val Tyr Gly Gly Gly Trp Trp Tyr Asn Asn Cys Gln Ala Ala Asn
                             805                 810                 815
```

```
Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
        835                 840                 845

Ala Asp Tyr Ser Leu Arg Ala Val Arg Met Lys Ile Arg Pro Leu Val
    850                 855                 860

Thr Gln
865

<210> SEQ ID NO 7
<211> LENGTH: 46
<212> TYPE: PRT
<213> ORGANISM: Homo sapiens

<400> SEQUENCE: 7

Thr Phe Pro Gly Phe Phe Ser Pro Met Leu Gly Glu Phe Val Ser Glu
1               5                   10                  15

Thr Glu Ser Arg Gly Ser Glu Ser Gly Ile Phe Thr Asn Thr Lys Glu
            20                  25                  30

Ser Ser Ser His His Pro Gly Ile Ala Glu Phe Pro Ser Arg
            35                  40                  45
```

HIGH SPECIFICITY MONOCLONAL ANTIBODY AGAINST A PROTEIN OR A POLYPEPTIDE HAVING OXIDATIVE MODIFICATION

CROSS-REFERENCE TO RELATED APPLICATION

This application claims priority to Japanese patent application Nos. 2008-264742 filed on Oct. 14, 2008, and 2008-330745 filed on Dec. 25, 2008, the disclosures of which are incorporated by reference herein in their entirety.

FIELD OF THE INVENTION

The present invention relates to a monoclonal antibody to an oxidatively modified protein or polypeptide.

DESCRIPTION OF RELATED ART

Pancreatic cancers are developed in the pancreas. It is known that 90% or more of them are pancreatic ductal cancers developed from cells associated with external secretion, in particular, cells of the pancreatic duct which transfers pancreatic fluid. Since the pancreas is surrounded by many organs such as stomach, duodenum, spleen, small intestine, large intestine, liver and gallbladder, it is very difficult to find pancreatic cancers. Meanwhile pancreatic cancers tend to spread to other organs at an early stage and tend to cause metastasis. Therefore, for therapy of pancreatic cancers, early detection is essential.

In general, a tumor marker, which enables diagnosis by blood test, is useful for early detection of cancers. As tumor markers for pancreatic cancers, CA19-9, CEA, Dupan-2, etc. are known. However, even if these are used as tumor markers, early detection of pancreatic cancers is difficult in many cases. Therefore, a new tumor marker for pancreatic cancers is profoundly desired.

Fibrinogen is glycoprotein transferred by blood and consists of 3 different polypeptide chains. When vascular disorder occurs, fibrinogen is cleaved by thrombin to form fibrin which is the main component of blood clot. Further, it is known that various cleavage products of fibrinogen and fibrin are involved in cell adhesion and cell dispersion, exhibit vasoconstrictor activity and chemotactic activity, and act as a mitogenic factor for several cell types. Moreover, it is known that the concentration of fibrinogen in plasma is associated with the risk of coronary artery disease (Non-patent Document 1: J. Thromb. Haemost. 4 (10), 2204-2209, 2006). Furthermore, it is known that mutation of the gene of fibrinogen α chain (α-fibrinogen) is involved in diseases such as dysfibrinogenemia, hypofibrinogenemia, afibrinogenemia and renal amyloidosis (Non-patent Document 2: Thromb. Haemost. 96 (2), 231-232, 2006; Non-patent Document 3: Blood 80 (8), 1972-1979, 1992).

Non-patent Document 1: J. Thromb. Haemost. 4 (10), 2204-2209, 2006

Non-patent Document 2: Thromb. Haemost. 96 (2), 231-232, 2006

Non-patent Document 3: Blood 80 (8), 1972-1979, 1992

SUMMARY OF THE INVENTION

The purpose of the invention is to provide an oxidatively modified protein or polypeptide-specific monoclonal antibody, which reacts with an oxidatively modified protein or polypeptide contained in plasma from a patient with pancreatic cancer, and which does not react with an unmodified protein or polypeptide, and a cell line producing the antibody. Another purpose of the present invention is to provide a method for detecting the protein or polypeptide, a detection reagent and the like.

In order to solve the above-described problems, the present inventors diligently made researches. By using a partial peptide of an oxidatively modified protein or polypeptide as an antigen, using a partial peptide of a non-oxidatively modified protein or polypeptide for screening, and by immunizing an high-affinity antibody-producing transgenic non-human mammal with the antigen, an antibody, which reacts with hydroxylated prolines present in a molecule of a protein or polypeptide, and which does not react with unmodified prolines, i.e., a monoclonal antibody, which realizes distinction between an oxidatively modified protein or polypeptide and an unmodified protein or polypeptide, was successfully obtained, and thus the present invention was achieved.

That is, the present invention is as follows:

(1) An antibody to a protein or polypeptide comprising an amino acid sequence in which a part of prolines in the molecule thereof are hydroxylated.

(2) The antibody according to item (1), wherein, in order to inhibit an immune reaction between a protein or polypeptide comprising an amino acid sequence in which a part of prolines in the molecule thereof are hydroxylated, which is solid-phased (solid-phase antigen) and an antibody to the solid-phase antigen, in a reaction system for a competitive reaction between a protein or polypeptide comprising an amino acid sequence in which a part of prolines in the analyte molecule are hydroxylated (antigen 1) and a protein or polypeptide comprising an amino acid sequence in which prolines in the analyte molecule are not hydroxylated (antigen 2), the antibody satisfies measurement conditions in which 50% inhibition activity to the immune reaction caused by the antigen 1 is at least 10-fold when compared to 50% inhibition activity to the immune reaction caused by the antigen 2.

(3) The antibody according to item (1) or (2), wherein the protein is fibrinogen.

(4) The antibody according to item (2), wherein the amino acid sequence of the antigen 2 is represented by TFPGFFSPMLGEFVSETESR (SEQ ID NO: 1) or ESSSHHPGIAEFPSR (SEQ ID NO: 2).

(5) The antibody according to item (2), wherein the solid-phase antigen and the amino acid sequence of the antigen 1 are represented by TFP(OH)GFFSPMLGEFVSETESR (SEQ ID NO: 3) or ESSSHHP(OH)GIAEFPSR (SEQ ID NO: 4) (P(OH) represents hydroxylated proline).

(6) The antibody according to any one of items (1) to (5), wherein the antibody is a monoclonal antibody.

The present invention also provides an antibody fragment derived from the above-described antibody.

(7) A monoclonal antibody to a protein or polypeptide comprising an amino acid sequence in which a part of prolines in the molecule thereof are hydroxylated, which is produced by a hybridoma whose accession number is FERM AP-21698.

(8) The monoclonal antibody according to item (7), wherein the amino acid sequence in which a part of prolines in the molecule thereof are hydroxylated is represented by TFP(OH)GFFSPMLGEFVSETESR (SEQ ID NO: 3) or ESSSHHP(OH)GIAEFPSR (SEQ ID NO: 4) (P(OH) represents hydroxylated proline).

(9) The antibody according to any one of items (1) to (8), which binds to a site to which the monoclonal antibody which is produced by the hybridoma whose accession number is FERM AP-21698 binds.

(10) A cell line which produces the monoclonal antibody according to any one of items (6) to (8).

(11) A cell line which produces an antibody to a protein or polypeptide comprising an amino acid sequence in which a part of prolines in the molecule thereof are hydroxylated, wherein the accession number of the cell line is FERM AP-21698.

(12) A method for detecting a protein or polypeptide comprising an amino acid sequence in which a part of a molecule is hydroxylated, wherein the antibody according to any one of items (1) to (9) is reacted with a biological sample to detect the protein or polypeptide.

(13) A method for detecting a fibrinogen comprising an amino acid sequence in which a part of prolines in the molecule thereof are hydroxylated, wherein the antibody according to item (3) is reacted with a biological sample to detect the fibrinogen.

(14) A method for detecting a protein or polypeptide comprising an amino acid sequence in which a part of prolines in the amino acid sequence of (a) or (b) below are hydroxylated, wherein the antibody according to item (4) is reacted with a biological sample to detect the protein or polypeptide:

(a)   TFPGFFSPMLGEFVSETESR   (SEQ ID NO: 1)
(b)   ESSSHHPGIAEFPSR        (SEQ ID NO: 2)

(15) A method for detecting a protein or polypeptide comprising the amino acid sequence of (c) or (d) below, wherein the antibody according to item (5) is reacted with a biological sample to detect the protein or polypeptide:

(c)   TFP(OH)GFFSPMLGEFVSETESR   (SEQ ID NO: 3)
(d)   ESSSHHP(OH)GIAEFPSR        (SEQ ID NO: 4)

(P(OH) represents hydroxylated proline)

(16) A detection reagent for a protein or polypeptide comprising an amino acid sequence in which a part of prolines in the molecule thereof are hydroxylated, the reagent comprising the antibody according to any one of items (1) to (9).

(17) The reagent according to item (16), wherein the protein is fibrinogen.

(18) The reagent according to item (16), wherein the protein or polypeptide comprising an amino acid sequence in which a part of prolines in the molecule thereof are hydroxylated comprises an amino acid sequence in which a part of prolines in the amino acid sequence of (a) or (b) below are hydroxylated:

(a)   TFPGFFSPMLGEFVSETESR   (SEQ ID NO: 1)
(b)   ESSSHHPGIAEFPSR        (SEQ ID NO: 2)

(19) The reagent according to item (16), wherein the protein or polypeptide comprising an amino acid sequence in which a part of prolines in the molecule thereof are hydroxylated comprises the amino acid sequence of (c) or (d) below:

(c) TFP(OH)GFFSPMLGEFVSETESR (SEQ ID NO: 3)
(d) ESSSHHP(OH)GIAEFPSR (SEQ ID NO: 4)
(P(OH) represents hydroxylated proline)

(20) A detection or diagnostic agent for cancer, comprising the antibody according to any one of items (1) to (9) or the reagent according to any one of items (16) to (19).

(21) The detection or diagnostic agent according to item (19), wherein the cancer is pancreatic cancer.

(22) A method for detecting cancer comprising using the antibody according to any one of items (1) to (9) or the reagent according to any one of items (16) to (19).

(23) The method according to item (22), wherein the cancer is pancreatic cancer.

According to the present invention, an oxidatively modified protein or polypeptide-specific antibody and a cell line producing the antibody are provided. Further, according to the present invention, a method for detecting an oxidatively modified protein or polypeptide, wherein the above-described antibody is reacted with a biological sample, and a reagent for detecting an oxidatively modified protein or polypeptide are provided.

The monoclonal antibody of the present invention which reacts with an oxidatively modified protein or polypeptide enables highly-sensitive and specific measurement of an oxidatively modified protein or polypeptide in an analyte such as blood and urine, and is preferably useful for diagnosis of cancers.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE INVENTION

Figure 1:
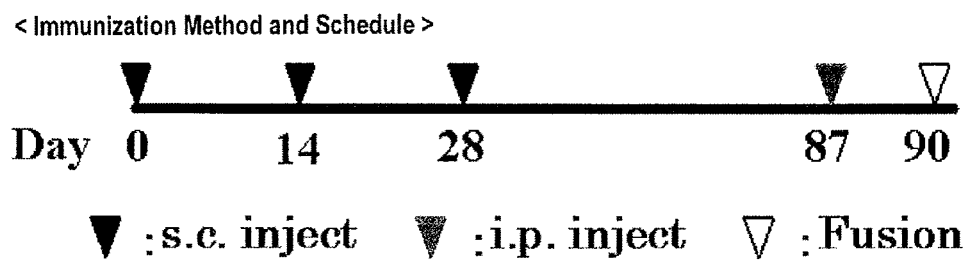
FIG. 1 shows the outline of an immunization method.

The present invention relates to an antibody which distinguishes a protein or polypeptide comprising an amino acid sequence in which proline is hydroxylated from a protein or polypeptide comprising an amino acid sequence in which proline is not hydroxylated and binds thereto.

The present inventors made an analysis of glycoprotein fractions which adsorb to concanavalin A extracted from plasma samples from a patient with pancreatic cancer and a healthy subject using the 2DICAL method (Ono et al., Mol. Cell Proteomics, 5, 1338, 2006) in which LC-MS data of the plurality of samples were compared to each other, and found two peptides which showed significant difference between the analytic value of the patient with pancreatic cancer and that of the healthy subject. The peptides found were ESSSHHP*GIAEFPSR (SEQ ID NO: 4) and TFP*GFFSPMLGEFVSETESR (SEQ ID NO: 3), both of which are derived from the sequence in α-fibrinogen. In these peptides, the seventh proline and the third proline are hydroxylated prolines (P*), respectively.

However, since the difference between these modified peptides and unmodified peptides is just a minor structural difference in which proline is hydroxylated or not, at present, there is no method for distinguishing modified peptides (peptides having hydroxylated proline) from unmodified peptides (peptides not having hydroxylated proline) and conducting a simple and easy measurement thereof.

According to the present invention, an antibody which may distinguish the above modified peptide and bind thereto is provided.

1. Antibody of the Present Invention

The antibody of the present invention is an antibody to an oxidatively modified protein or polypeptide comprising an amino acid sequence in which in an amino acid sequence in a protein or polypeptide molecule, at least a part of amino acid residue are hydroxylated (oxidatively modified). In a more preferred embodiment, the antibody of the present invention is a high-affinity antibody which specifically binds to a partial fragment or full-length protein comprising an amino acid sequence in which in an amino acid sequence of fibrinogen α (referred to as "FGA"), a part of proline residues are hydroxylated (referred to as "oxidatively modified FGA") (hereinafter also referred to as "anti-oxidatively modified FGA antibody"). In a preferred embodiment of the present invention, in order to prepare the antibody of the present invention, as an animal to be immunized, a transgenic non-human mammal having high-affinity antibody-producing ability called "GANP (registered trademark)" is used.

The GANP (registered trademark) transgenic non-human mammal is a non-human mammal into which a gene encoding Germinal center-associated nuclear protein is introduced, and when immunizing the animal with a given antigen, the animal can produce a high-affinity antibody to the antigen (International Publication WO 00/50611 pamphlet; Sakaguchi N. et al., J Immunol. Apr. 15, 2005 174 (8): 4485-94).

For example, a GANP transgenic non-human mammal (e.g., mouse) can be prepared using the method described in the above-described pamphlet or document of Sakaguchi et al. Alternatively, a commercially-available GANP (registered trademark) mouse (TransGenic Inc.) can be obtained.

In the method for obtaining the monoclonal antibody ("anti-oxidatively modified FGA antibody") of the present invention, firstly, an animal such as a GANP transgenic non-human mammal is immunized with a partial peptide of oxidatively modified FGA, an antibody-producing cell (e.g., B cell) is collected from the immunized animal, and the antibody-producing cell is fused with a myeloma cell to prepare a hybridoma (fusion cell line). By collecting an antibody produced by the hybridoma, the monoclonal antibody of interest can be obtained.

The anti-oxidatively modified FGA antibody is called "hapten antibody". When preparing such a hapten antibody, the molecular structure design of a hapten-carrier complex significantly affects the performance of a specific antibody.

2. Preparation of Antigen

Oxidatively modified FGAs highly exist in plasma from patients with pancreatic cancer. Even if a FGA from a genetically-modified product or FGA from plasma of normal human is obtained, it cannot be used as an antigen since it is not oxidatively modified. Therefore, it is necessary to synthesize an immunogen comprising an oxidatively-modified amino acid sequence.

In the present invention, a partial peptide of oxidatively modified FGA is synthesized to be used as an immunogen. However, since a synthetic peptide is a low-molecular-weight substance, when a mouse is immunized with the peptide as it is, it is difficult to obtain an antibody. Therefore, the synthetic peptide and a carrier protein are subjected to the formation of disulfide bond using the MBS method to prepare an immunogen.

In the present invention, an immunogen can be prepared according to the known method (Fmoc method, Kunio Fujiwara et al., Journal of Immunological Methods, 61, 217-226 (1983)).

Chemical synthesis of peptides can be conducted according to methods known in the art such as the Fmoc method (fluorenyl methyloxy carbonyl method) and tBoc method (t-butyloxycarbonyl method).

As a carrier protein, BSA, KLH (Keyhole Limpet Hemocyanin), OVA (Ovalbumin), etc. can be used. Those skilled in the art would be able to prepare an immunogen according to the known method.

The amino acid sequence that is the basis for synthesis of antigen peptide is an amino acid sequence of FGA (SEQ ID NO: 5 or 6), and in the amino acid sequence, an amino acid sequence consisting of any contiguous 10 to 50 amino acids, preferably 10 to 30 amino acids, and more preferably 15 to 20 amino acids is selected. As a selection criterion, at least one proline must be included in the amino acid sequence. Such amino acid residues are oxidized to synthesize an oxidatively modified peptide.

The region that can be used as an antigen is preferably a region at positions 528-573 of the amino acid sequence represented by SEQ ID NO: 5 or 6, "TFPGFFSPM-LGEFVSETESRGSESGIFTNTKESSSHHPGIAEFPSR" (SEQ ID NO: 7), and amino acid residues to be oxidatively modified are prolines.

For example, for the purpose of obtaining an antibody to a protein or polypeptide derived from a patient with pancreatic cancer, it is sufficient to oxidize at least one proline residue in an antigen molecule.

In a method for synthesis of an oxidatively modified peptide, e.g., addition of a hydroxyl group to a proline residue, in the process of chemical synthesis in which the length of amino acid residues is extended by adding residues one by one, a hydroxyproline is bound thereto instead of a proline residue. As a method for synthesizing a peptide to be used as an antigen, methods well known in the art, e.g., the solid-phase synthesis method and the liquid-phase synthesis method can be employed. A commercially-available peptide synthesis apparatus (e.g., Shimazu PSSM-8) may also be used.

Examples of amino acid sequences of antigen peptide obtained in such a way are as follows:

| (a) | TFPGFFSPMLGEFVSETESR | (SEQ ID NO: 1) |
| (b) | ESSSHHPGIAEFPSR | (SEQ ID NO: 2) |

The above-described amino acid sequence in (a) consists of 20 amino acids, and an amino acid at the third position or proline at the eighth position or both of them are oxidized.

The above-described amino acid sequence in (b) consists of 15 amino acids, and an amino acid at the seventh position or proline at the thirteenth position or both of them are oxidized.

An amino acid sequence in which an amino acid at the third position of the amino acid sequence in (a) is oxidized and an amino acid sequence in which an amino acid at the seventh position of the amino acid sequence in (b) is oxidized are shown in items (c) and (d) below, respectively.

(c) TFP(OH)GFFSPMLGEFVSETESR (SEQ ID NO: 3)

(d) ESSSHHP(OH)GIAEFPSR (SEQ ID NO: 4)

In the amino acid sequence in (c) or (d) above, "P(OH)" means hydroxylated proline.

3. Immunization with Antigen and Measurement of Antibody Level

Examples of animals to be immunized include GANP transgenic non-human mammals (International Publication WO 2004/040971 pamphlet). The type of non-human mammal is not particularly limited. Examples thereof include mouse, rat, rabbit, etc., and mouse is preferred.

The administration amount of the antigen per animal is 10 to 2000 µg in total. At the time of immunization with the antigen, in general, an adjuvant is mixed with an antigen solution. Examples of adjuvants include Freund's complete adjuvant (FCA), Freund's incomplete adjuvant (FIA), and aluminum hydroxide adjuvant. Immunization is mainly conducted by intravenous injection, subcutaneous injection, intraperitoneal injection, intramuscular injection, subcutaneous injection in foodpad or the like. The immunization interval is not particularly limited, and is several days to several weeks, and preferably 2 to 3 weeks. The number of times of immunization is 1 to 10, and preferably 2 to 5.

After the antibody level is increased by immunization by 2 or more of the absorbance value, the animal is left for 2 to 6 months, preferably 4 to 6 months, and more preferably 6 months, until the antibody level is decreased by 0.05 to 1, preferably 0.05 to 0.5, and more preferably 0.05 of the absorbance value. The dilution degree of serum which exhibits the absorbance value is, for example, 27,000-fold.

When immunizing a GANP transgenic non-human mammal, immunization may be conducted from start to finish without the necessity of decrease in the level of absorbance, employing an immunization interval in a general method for preparing a monoclonal antibody.

The antibody level can be checked using blood collected from the immunized animal. Preferably, the collected blood is not stored at a lower temperature after collection of blood but is immediately centrifuged to separate serum. The obtained serum is subjected to serial dilution, and thereby the antibody level can be measured by means of ELISA (enzyme-linked immunosorbent assay), EIA (enzyme immunoassay), RIA (radioimmuno assay), etc. When measuring the antibody level by means of ELISA or EIA, the absorbance can be measured using a spectrophotometer.

According to results of the measurement, an animal exhibiting a higher antibody level with respect to the oxidatively modified FGA is subjected to the final immunization. Note that immunization of antigens and measurement of antibody levels are not limited to the above-described measurement method.

Several days, preferably 3 to 5 days after the final immunization, an immunocompetent cell (e.g., spleen cell) is isolated. When an antigen is injected subcutaneously in the foodpad of the animal, the final immunization is conducted once, and 7 to 13 days, preferably 8 to 10 days after the immunization, an immunocompetent cell such as a spleen cell or associated lymph node is isolated. Collection of blood is conducted 1 to 4 weeks, preferably 1 to 2 weeks after the immunization.

In the present invention, in order to obtain a polyclonal antibody, collection of blood is conducted on a day on which a desired antibody level as described above is exhibited to obtain antiserum. When an antibody must be purified, such purification can be made using a known method suitably selected from ammonium sulfate precipitation, ion exchange chromatography, gel filtration chromatography, affinity chromatography, etc., or using a combination thereof. After that, the reactivity of the polyclonal antibody in antiserum is measured using the ELISA method or the like.

4. Preparation of Monoclonal Antibody to Oxidatively Modified FGA

Hereinafter, the method for preparing a monoclonal antibody to oxidatively modified FGA will be described, but the present invention is not limited thereto.

(1) Preparation of Antibody-Producing Cell

An antibody-producing cell is prepared from a spleen cell, etc. or associated lymph node, etc., of an animal such as a GANP transgenic non-human mammal which is immunized. Examples of lymph nodes include groin lymph node and mediastinal lymph node. It is not necessary to particularly conduct operation to separate antibody-producing cells from a cell population collected, but it is desirable to separate only antibody-producing cells from the cell population. Further, at the time of preparation of antibody-producing cells, tissue debris and erythrocytes are preferably removed in advance as much as possible. As a method for removing erythrocytes, a method using a commercially-available solution for erythrocyte removal or a method in which a neutral buffer prepared from ammonium chloride and Tris is prepared and used is preferably employed. The state of the prepared antibody-producing cells may be deteriorated unless a next operation is conducted immediately after the preparation. Therefore, when it takes time to move on to the next operation after the preparation, the cells are preferably kept still on ice.

(2) Cell Fusion

Cell fusion is performed by fusing the above-described antibody-producing cells and myeloma cells in order to prepare a cell (hybridoma), which continues to proliferate semi-permanently, producing antibodies. As the myeloma cell to be fused with the antibody-producing cell, a generally available cell line of an animal such as mouse can be used. The cell line to be used is preferably characterized in that it cannot survive in a HAT selection medium (medium containing hypoxanthine, thymidine and aminopterin) and can only survive in the state of being fused with the antibody-producing cell. Examples of myeloma cells include P3X63-Ag.8.U1 (P3UI) and P3/NS I/1-Ag4-1 (NS I).

In a commercially-available medium such as DMEM or RPMI1640 medium in which fetal bovine serum (FCS), etc., are not contained, $1 \times 10^6$ to $1 \times 10^7$/mL of pancreatic cells and/or lymph node cells are mixed with $1 \times 10^5$ to $1 \times 10^6$/mL of myeloma cells (the ratio of the spleen cells and/or lymph node cells to the myeloma cells is preferably 5:1), and cell fusion is performed in the presence of a cell fusion promoter. Examples of cell fusion promoters include polyethylene glycol having the average molecular weight of 200 to 20000 dalton.

Cell fusion can also be performed using a commercially-available cell fusion apparatus utilizing electrical stimulation (e.g., electroporation). Cell fusion can also be performed using Sendai virus. Those skilled in the art would be able to fuse the above-described antibody-producing cell and the myeloma cell using a known cell fusion method.

After cell fusion, cells are diluted using a HAT medium which is prepared using, for example, a 10 to 20% (preferably 20%) FCS-containing RPMI1640 medium. After that, 0.5 to $3 \times 10^5$ cells are seeded in each well of a 96-well culture plate, and it is cultured in a $CO_2$ incubator.

(3) Establishment of Hybridoma

Next, hybridomas which produce an antibody of interest are selected from cells after the cell fusion treatment. 10 to 14 days after the cell fusion, a colony is formed by the selected cells in a HAT medium as described above. Culture supernatant in each well of the colony-positive 96-well culture plate is collected, and the antibody level to oxidatively modified FGA is confirmed. Confirmation is made by means of enzyme immunoassay (ELISA), radioimmunoassay (RIA) or the like. Antibodies produced from the cells include antibodies to KLH and BSA, which are carrier proteins. By measuring the antibody level to KLH, etc., BSA antibody-positive wells exhibiting a higher antibody level to KLH, etc. can be excluded. After confirming positive wells in which cells produce antibodies to oxidatively modified FGA, the cells are transferred to a 24-well or 12-well culture plate.

In this regard, the medium is preferably replaced by a HT medium in which aminopterin is excluded (medium containing hypoxanthine and thymidine). That is because, since aminopterin is a substance which inhibits DNA replication in cells, when aminopterin in a medium is removed but remains in cells, DNA replication in cells does not occur in the absence of hypoxanthine and thymidine. After culture for a while in the HT medium, the antibody level in the culture supernatant is confirmed again. Hybridomas are unstable since they are fused cells, and there is a high possibility that antibody production disappears a short time later. Therefore, it is preferred to confirm the antibody level of the second time. As described above, in the present invention, it is required to obtain hybridomas having a high specificity to oxidatively modified FGA. Therefore, it is important to confirm the cross-reactivity with other unmodified FGAs on the culture supernatant by means of ELISA, RIA or the like.

Cells in the finally selected well are subjected to cloning to obtain a single cell. In cloning, for example, a cell suspension is suitably diluted with a 10 to 20% (preferably 20%) FCS-containing RPMI1640 medium, and after that, cells are seeded in a 96-well culture plate in a manner in which 0.3 to 2 cells are put into each well thereof. Regarding the number of cells to be put into each well of the 96-well culture plate, in order to obtain a high probability that the number of cells present in one well is 1, cells are preferably seeded in a manner in which one cell is put into each well. 7 to 10 days after seeding the cells, culture supernatant in a colony-positive well is collected. It is preferred to confirm whether or not it is a single colony 3 to 5 days after the seeding. The antibody level of the collected culture supernatant is checked. Again, a clone which exhibits a high specificity to oxidatively modified FGA and a low cross-reactivity with unmodified FGA is selected. In addition, the cell in the selected well is proliferated to some extent to establish a hybridoma line. Cloning may be performed several times according to need.

(4) Preparation of Monoclonal Antibody

An oxidatively modified FGA-specific monoclonal antibody is purified and prepared from the established hybridoma line using a method such as: a method for preparing an antibody from a culture supernatant cultured in a medium in which the serum concentration is reduced; a method for preparing an antibody from a culture supernatant cultured in a commercially-available serum-free medium; and a method for preparing an antibody, wherein a hybridoma is intraperitoneally injected to an animal, peritoneal fluid of the animal is collected, and the antibody is prepared from the peritoneal fluid. A culture supernatant is collected from a culture in which 0.1 to $4\times10^5$/mL of cells are prepared and culture thereof is performed for 1 to 2 weeks. In the case of peritoneal fluid, 0.1 to $1\times10^7$ hybridomas are intraperitoneally administered to an animal belonging to the same species of the mammal from which the myeloma cell is derived, and the hybridomas are subjected to mass propagation. 1 to 2 weeks after that, peritoneal fluid is collected.

Examples of culture methods include: a method using a culture flask; a method using a spinner flask; a method using a shaker flask; and a method using a bioreactor. Examples of methods for purifying antibodies include: a purification method using a protein G affinity column or protein A affinity column; a purification method using an oxidatively modified FGA affinity column; a method of purification from ammonium sulfate fractions by means of gel filtration chromatography; and a purification method using ion exchange chromatography. Purification can be performed by suitably selecting one of these known methods or using a combination thereof. When purifying mouse $IgG_1$ using a protein A affinity column, use of a buffer or the like in which binding conditions are optimized is effective. Those skilled in the art would be able to perform purification by suitably selecting optimum conditions.

"Anti BP-FGA MAb Clone: 11A5", which is a cell line (hybridoma) producing the monoclonal antibody of the present invention, was deposited to International Patent Organism Depositary, National Institute of Advanced Industrial Science and Technology (Chuo 6, Higashi 1-1-1, Tsukuba-shi, Ibaraki 305-8566) on Oct. 7, 2008. The accession number thereof (described in the receipt) is "FERM AP-21698". "FERM AP-21698" is a clone established as "11A5" in Example 1. Thereafter, the hybridoma cell line was transferred to a deposit under the Budapest Treaty from the national deposit. Said hybridoma cell line now has another Accession No., TERM BP-11163, which was provided by the IDA.

Further, as the monoclonal antibody of the present invention, an antibody that binds to a site which a monoclonal antibody produced by the hybridoma whose accession number is FERM AP-21698 binds to (recognizes) (e.g., an epitope comprising the amino acid sequence represented by SEQ ID NO: 3 or 4) is preferred.

(5) Properties of Monoclonal Antibody

The monoclonal antibody of the present invention specifically binds to an oxidatively modified protein or polypeptide and exhibits high affinity. The affinity satisfies the conditions in which 50% inhibition activity in the case of competitive inhibition caused by addition of an oxidatively modified antigen to a reaction system of a solid-phased antigen and an antibody is at least 10-fold when compared to 50% inhibition activity in the case of competitive inhibition caused by addition of a non-oxidatively modified antigen to the reaction system.

For example:
(i) Firstly, a protein or polypeptide comprising an amino acid sequence in which a part of prolines in the molecule thereof are hydroxylated is immobilized to a solid phase in a measurement system (an antigen which is solid-phased is called "solid-phase antigen").
(ii) Next, in order to inhibit an immune reaction with an antibody to the solid-phase antigen, a protein or polypeptide comprising an amino acid sequence in which a part of prolines in the analyte molecule are hydroxylated (referred to as "antigen 1") and a protein or polypeptide comprising an amino acid sequence in which prolines in the analyte molecule are not hydroxylated (referred to as "antigen 2") are subjected to a competitive reaction.

The antigen molecule (solid-phase antigen) in the antigen-antibody reaction in (i) above has an amino acid sequence in which prolines are hydroxylated, and the monoclonal antibody of the present invention specifically binds to the solid-phase antigen comprising the hydroxylated prolines. When a protein or polypeptide having an amino acid sequence, which is identical to that of the solid-phase antigen, and whose hydroxylated sites are identical to those of the solid-phase antigen (antigen 1), is added to the reaction system, the monoclonal antibody binds to the antigen 1, and as a result, binding between the solid-phase antigen and the antibody is competitively inhibited.

When a protein or polypeptide, which has an amino acid sequence identical to that of the solid-phase antigen, but which does not have any hydroxylated amino acid (antigen 2), is added to the above-described reaction system, the monoclonal antibody binds to the antigen 2, and as a result, binding between the solid-phase antigen and the antibody is competitively inhibited.

The antibody of the present invention satisfies the measurement conditions in the competitive inhibition test in which 50% inhibition activity to the immune reaction caused by the antigen 1 is at least 10-fold, preferably at least 20-fold, more preferably at least 50-fold, even more preferably at least 100-fold, still more preferably at least 200-fold, still even more preferably at least 500-fold, and particularly preferably at least 1000-fold when compared to 50% inhibition activity to the immune reaction caused by antigen 2, and has extremely high affinity to the antigen 1.

(6) Antibody Fragment

Fragments of the above-described antibody are also included in the antibody of the present invention. Like the antibody of the present invention, the antibody fragment of the present invention has binding activity to a protein or polypeptide comprising an amino acid sequence in which a part of prolines in the molecule thereof are hydroxylated, and has the above-described properties.

The antibody fragment refers to a partial region of the antibody of the present invention. Examples thereof include Fab, Fab' and F(ab')$_2$. The above-described antibody fragment can be obtained by cleaving the antibody of the present invention using various proteolytic enzymes depending on purposes.

For example, Fab and F(ab')$_2$ can be obtained by treating the antibody molecule with papain and pepsin, respectively. Further, Fab' can be obtained by breaking the disulfide bond in the hinge region of the above-described F(ab')$_2$.

5. Detection Method

Oxidatively modified FGA can be utilized as a clinical marker for cancers (tumor marker). By reacting the antibody of the present invention with a biological sample and measuring oxidatively modified FGA in the biological sample, tumors can be detected or diagnosed using the measurement result as an index.

Therefore, the present invention provides a method for detecting a protein or polypeptide comprising an amino acid sequence in which a part of the molecule thereof is hydroxylated or a method for detecting or diagnosing a cancer, wherein the antibody of the present invention is reacted with a biological sample to detect the protein or polypeptide. Examples of proteins to be targeted for detection include fibrinogen. Examples of polypeptides to be targeted for detection include a polypeptide comprising an amino acid sequence in which a part of prolines in the amino acid sequence of (a) or (b) below are hydroxylated, and preferably a polypeptide comprising the amino acid sequence of (c) or (d) below:

(a) TFPGFFSPMLGEFVSETESR (SEQ ID NO: 1)
(b) ESSSHHPGIAEFPSR (SEQ ID NO: 2)
(c) TFP(OH)GFFSPMLGEFVSETESR (SEQ ID NO: 3)
(d) ESSSHHP(OH)GIAEFPSR (SEQ ID NO: 4)

(P(OH) represents hydroxylated proline.)

Measurement of oxidatively modified FGA can be conducted using one of methods known as hapten immunoassay methods generally used (e.g., ELISA and EIA), and there is no limitation.

Cancer is not particularly limited in the present invention. Examples thereof include at least one type of cancer selected from the group consisting of brain tumor, esophageal cancer, pharyngeal cancer, tongue cancer, lung cancer, gastric cancer, small intestine or duodenal cancer, large intestine cancer, urinary tract malignancy (e.g., prostate cancer, kidney cancer, bladder cancer, testicular tumor), pancreatic cancer, liver cancer, prostate cancer, breast cancer, uterine cancer, ovarian cancer, thyroid gland cancer, gallbladder cancer, biliary cancer, sarcoma (e.g., osteosarcoma and myosarcoma) and melanoma. One type of cancer or 2 or more types of cancers in combination may be targeted for detection.

In particular, fibrinogen derived from a patient with pancreatic cancer comprises the amino acid sequence of peptide (peptide in which prolines are hydroxylated) represented by SEQ ID NO: 3 or 4. Therefore, the antibody of the present invention, which specifically binds to the amino acid sequence, is particularly preferred for detecting pancreatic cancers.

A biological sample is collected from a subject such as a patient with cancer, a patient suspected of having cancer or a person having a physical examination to prepare an oxidatively modified FGA measurement sample. Examples of biological samples include blood, tissue, etc. In the case of blood, it is preferred that it is centrifuged after collection to separate plasma and that the obtained plasma is used.

Next, the aforementioned measurement sample is reacted with the antibody of the present invention. The detection of oxidatively modified FGA can be performed by means of ELIZA, which is generally employed. As a matter of convenience, in the explanation herein, a mouse-derived antibody is used as the antibody of the present invention.

In the measurement by means of ELIZA, firstly, a microplate is coated with an anti-oxidatively modified FGA antibody (Clone: 11A5) as a capture antibody. Next, a biological sample (analyte) is added to wells on the plate. The oxidatively modified FGA binds to the anti-oxidatively modified FGA antibody (Clone: 11A5) on the plate. After the plate is washed, an HRP-labeled anti-FGA antibody (Clone: 1E9) as a detection antibody is added to the plate, and it is reacted with the oxidatively modified FGA on the plate. Finally, the oxidatively modified FGA in the biological sample is quantified by chromogenic reaction catalyzed by HRP. Other than HRP (peroxidase), alkaline phosphatase, malate dehydrogenase, α-glucosidase, α-galactosidase, etc. can also be used as a labeling enzyme in the detection antibody. In the case of sandwich ELISA, the more the amount of oxidatively modified FGA in the biological sample is, the greater the measurement values of the amounts of color development, fluorescence, luminescence, etc. are.

6. Method for Assessing Cancer

According to the present invention, the status of cancer can be assessed utilizing detection results obtained by the detection method described in item 5 above as indexes. When a detection result exceeds a predetermined reference value, it is regarded as oxidatively modified FGA-positive, and when a detection result is equal to or lower than the predetermined reference value, it is regarded as oxidatively modified FGA-negative. When a result is positive, it is judged that there is a possibility of cancer development. Thus, the state of cancer can be assessed. The predetermined reference value is suitably set depending on the type of cancer.

The state of cancer means the presence/absence or degree of progression of cancer or tumor. Examples thereof include presence/absence of cancer development, degree of progression of cancer, degree of malignancy of cancer, presence/absence of metastasis of cancer, presence/absence of cancer recurrence, etc. In the above-described assessment, one of the states of cancer or a plurality of the states of cancer in combination may be suitably selected. In order to assess the presence/absence of cancer, whether or not a subject is affected with cancer is judged. The grade of malignancy of cancer indicates the degree of the development of cancer. Evaluation can be made using stage classification. Further, so-called early stage cancer and advanced-stage cancer can be classified and evaluated. Metastasis of cancer is evaluated by whether or not neoplasm is developed at a region which is remote from the position of the primary tumor. Cancer recurrence is evaluated by whether or not cancer reappears after the interval stage or remission.

7. Kit and Reagent Including the Antibody of the Present Invention

In the present invention, an antibody to oxidatively modified FGA can be used as a kit or reagent for detecting oxidatively modified FGA. The kit or reagent of the present invention can be used for detecting the above-described tumors, etc.

When using the antibody (e.g., monoclonal antibody) of the present invention as an agent for detecting or diagnosing cancer, the monoclonal antibody can be combined with other solvents and solutes to provide a composition. For example, the antibody can be combined with distilled water, a pH buffer reagent, salt, protein, a surfactant, etc. Further, the monoclonal antibody can be used after enzyme labeling. Examples of labeling enzymes include HRP (horseradish peroxidase), alkaline phosphatase, malate dehydrogenase, α-glucosidase, α-galactosidase, gold colloid, etc.

In addition to the antibody of the present invention, the kit of the present invention may include the above-described solvents and solutes, an enzyme labeling reagent, an antigen-immobilized microplate, an antibody-diluted solution, an OPD (ortho-phenylenediamine) tablet, a substrate liquid, a solution for reaction termination, a concentrated wash solution, an instruction, etc. The kit of the present invention may also include reaction media such as a buffer solution which provides optimum conditions for reaction, a buffer solution which is useful for stabilization of a reaction product, and an agent for stabilization of a reacting substance.

Hereinafter, the present invention will be described in more detail based on working examples and experimental examples. However, the present invention is not limited thereto.

Example 1

Preparation of Monoclonal Antibody Specific to Oxidatively Modified FGA (1) Preparation of Antigen Oxidatively modified FGA only exists in serum from patients with pancreatic cancer. Even if a FGA product produced by genetic recombination or a FGA from normal human serum is obtained, it is not oxidatively modified. Therefore, an immunizing antigen including an oxidatively modified sequence was chemically synthesized.

Next, a partial peptide of the synthesized oxidatively modified FGA was used as an immunizing antigen.

A synthetic peptide and a carrier protein, Keyhole Limpet Hemocyanin (KLH) were subjected to disulfide binding using the MBS method to prepare an immunizing antigen.

(2) Immunization of Mouse

FIG. 1 shows the outline of an immunization method. Immunization was performed as described below. A prepared immunogen (1 mg/mL) was mixed with FCA which was equal in quantity to form an emulsion. This was administered to a mouse subcutaneously in a region of the back (each time 100 μL). After that, 50 μL of emulsion formed by mixing the immunogen (1 mg/mL) with FIA which was equal in quantity was repeatedly administered to the mouse subcutaneously in the region of the back at a 2-week interval. Antigen administration was performed three times in total. The antibody level was confirmed by ELISA. With respect to a case showing high antibody level, 50 μL of immunogen (1 mg/mL) was finally administered to the mouse intraperitoneally. Three days later, spleen was removed for cell fusion.

(3) Preparation of Spleen Cells and Cell Fusion

The removed spleen was mashed, and spleen cells including anti-oxidatively modified FGA antibody-producing cells were prepared. In the both immunization methods, about $1 \times 10^8$ spleen cells per mouse were successfully prepared. Meanwhile P3U1 (myeloma cell) was cultured to prepare P3U1 whose ratio of living cells on the cell fusion day was 95% or higher. The spleen cells and P3U1s were mixed together (5:1), and cell fusion was performed using polyethylene glycol having the concentration of 50% and the molecular weight of 1,450. After that, the obtained cells, which were washed with a medium and suspended in a HAT medium, were seeded in each well of a 96-well culture plate in a manner in which each well had $1 \times 10^5$ cells.

(4) Screening of Antibody-Producing Positive Well

After cell fusion, culture supernatant on day 10 was collected, and screening of antibody-producing positive well was performed using the method of Experimental Example 1 described later. Among 2200 wells, 2 wells were oxidatively modified FGA-positive and unmodified FGA-negative. Cells of these selected wells were transferred to a 24-well plate, cultured for 1 to 2 days, and screening was performed again using the method of Experimental Example 1. Finally, 2 wells were oxidatively modified FGA-positive.

(5) Cloning

Cells of the two wells showing high specificity to oxidatively modified FGA were subjected to cloning using the limiting dilution method. Concretely, cells were prepared using a RPMI medium containing 10% FCS (5 cells/mL), and 200 μL thereof was added to each well of two 96-well culture plates. 10 days later, the antibody level with respect to oxidatively modified FGA in culture supernatant was measured using the method of Experimental Example 1 described later. It was confirmed that it was positive, and clones derived from the respective wells were obtained. They were antibodies having the sufficient specificity of interest of the present invention. The established clones were named "11A5" and "11G7", respectively (FIG. 2).

Figure 2:
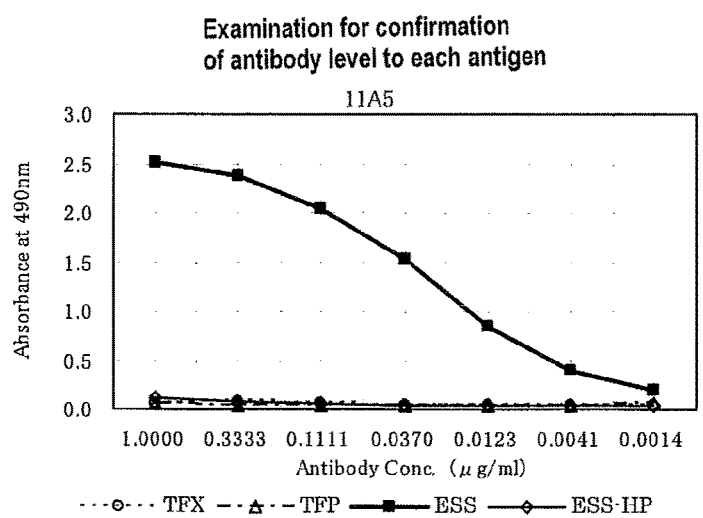
FIG. 2 shows examination results of confirmation of specificity of monoclonal antibodies derived from clones 11A5 and 11G7 to oxidatively modified FGA.
Figure 2:
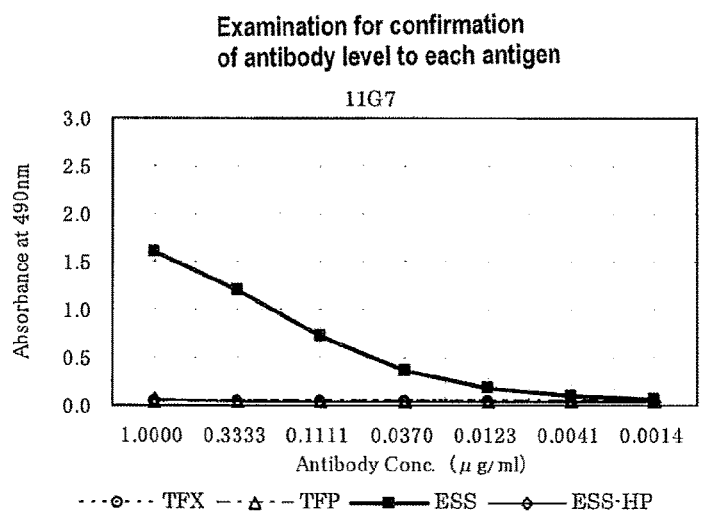

In FIG. 2, each of the synthetic peptides TFP (SEQ ID NO: 1), ESS-HP (SEQ ID NO: 2), TFX (SEQ ID NO: 3) and ESS (SEQ ID NO: 4) were used as solid-phased antigens, and as a result, reactivity was observed only in the case of ESS (SEQ ID NO: 4). Regarding the other peptides, no reactivity was observed.

EXPERIMENTAL EXAMPLE 1

Method for Screening Antibody

To each well of a 96-well microtiter plate, two types of oxidatively modified FGA peptides prepared using PBS (pH 7.0) (1 μg/mL) were added as solid-phased antigens (50 μL each), and left at 25° C. for 1 hour. At the same time, 2 types of unmodified FGAs were added in the same way (50 μL each) for confirmation of specificity, and left at 25° C. for 1 hour. Next, the plate was washed with PBS containing 0.05% Tween20 (pH 7.0) (PBST) 3 times. After that, 200 μL of PBST containing 0.5% gelatin (blocking solution) was added to each of the wells, and kept at 25° C. for 1 hour. After washing, 50 μL of culture supernatant was added to each of the wells, and kept at 25° C. for 1 hour. Next, after washing with PBST 3 times, 50 μL of 2500-fold diluted HRP-labeled anti-mouse IgG antibody (ZYMED) was added to each of the wells, and kept at 25° C. for 1 hour. Next, after washing with PBST 3 times, 100 μL of o-phenylenediamine solution prepared using 0.1 M citrate-phosphate buffer solution (pH 5.0) containing 0.02% hydrogen peroxide (0.5 mg/mL) was added to each of the wells, and kept at 25° C. for 10 minutes. After that, 100 μL of 1M sulfuric acid solution was added to each of the wells to terminate color reaction. After that, absorbance at 490 nm was measured using an ELISA reader.

(6) Purification of Antibody

The monoclonal antibodies of interest were purified from the above-described two clones using the following method. Firstly, the established clones were suspended in a commercially-available serum-free medium (Hybridoma SFM: Invitrogen) for preparation ($4 \times 10^5$ cells/mL). 50 mL of the cell-suspended solution was put into a T225 flask, and cultured at 37° C. under 5.0% $CO_2$ atmosphere for about a week. After that, culture supernatant was collected. The collected culture supernatant was applied to a protein G column and eluted with glycine buffer (pH 3.0) to purify the monoclonal antibody.

After that, examination for confirming specificity to oxidatively modified FGA was performed again using the method of Experimental Example 1.

The result thereof was similar to that of the culture supernatant (FIG. 2).

(7) Examination of Crossreactivity of the Established Clones

Figure 3:
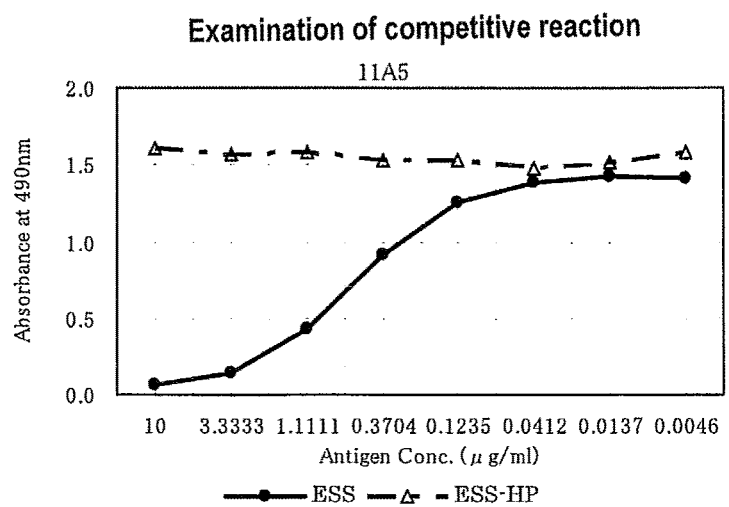
FIG. 3 shows examination results of crossreactivity of monoclonal antibodies derived from clones 11A5 and 11G7 to oxidatively modified FGA.
Figure 3:
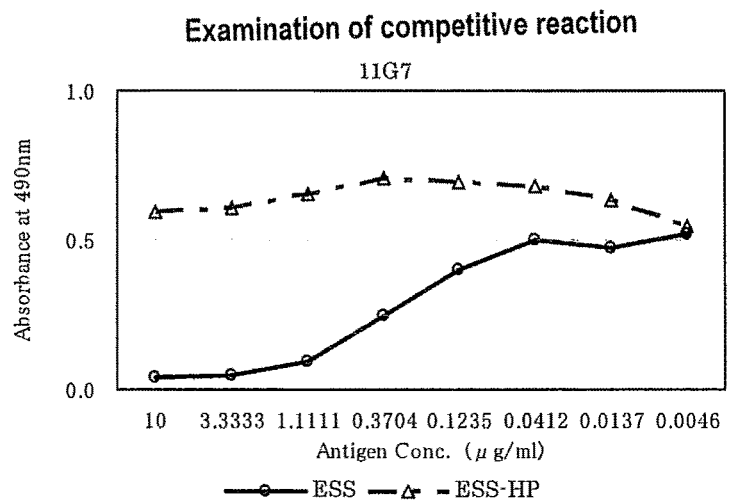

With respect to the above-described two clones which recognize oxidatively modified FGA, examination of crossreactivity of the antibodies to non-oxidatively modified FGA was performed using the method of Experimental Example 2 described below. 50% inhibitory concentration of ESS (SEQ ID NO: 4) was about 0.4 μg/ml, and it was at least 25 times as much as that of ESS-HP (SEQ ID NO: 2) (FIG. 3).

EXPERIMENTAL EXAMPLE 2

Examination of Crossreactivity

The antibody level in the diluted culture supernatant was measured using the method of Experimental Example 1. According to the result thereof, the dilution ratio was determined so that the absorbance at 490 nm became 1. 70 μL of culture supernatant, which was diluted on a dilution plate employing the above-described determined dilution ratio, and each of 70 μL of oxidatively modified FGA peptide solutions, which were prepared in a stepwise manner to have various concentrations, were mixed together and added to respective wells, and kept at 25° C. for 30 minutes for prereaction. Next, reaction solutions (50 μL each), which were prereacted with the respective wells of the plate subjected to blocking treatment using the method of Experimental Example 1, were added to the respective wells, and kept at 25° C. for 1 hour. Next, after washing with PBST 3 times, 50 μL of 2500-fold diluted HRP-labeled anti-mouse IgG antibody (ZYMED) was added to each of the wells, and kept at 25° C. for 1 hour. Next, after washing with PBST 3 times, 100 μL of o-phenylenediamine solution prepared using 0.1 M citrate-phosphate buffer solution containing 0.02% hydrogen peroxide (pH 5.0) (0.5 mg/mL) was added to each of the wells, and kept at 25° C. for 10 minutes. After that, 100 μL of 1M sulfuric acid solution was added to each of the wells to terminate color reaction. After that, absorbance at 490 nm was measured using an ELISA reader.

EXPERIMENTAL EXAMPLE 3

Confirmation of Expression of 565HP-α-Fibrinogen Using many Clinical Analytes α-fibrinogen which is recognized by 11A5 is designated as "565HP-α-fibrinogen". Employing a competitive ELISA method using 11A5, blood samples of 701 cases of various pathological conditions shown in Table 1 were subjected to examination of expression of 565HP-α-fibrinogen.

TABLE 1

| | | Healthy subjects | Ductal pancreatic cancer | Other pancreatic cancers | Chronic pancreatitis | Benign pancreas tumor | Bile duct cancer | Cholecystitis | Liver cancer | Esophageal cancer | Gastric cancer | Large intestine cancer | Total |
|---|---|---|---|---|---|---|---|---|---|---|---|---|---|
| number of cases | | 113 | 160 | 15 | 12 | 38 | 25 | 22 | 14 | 10 | 147 | 145 | 701 |
| Sex | M | 73 | 95 | 9 | 9 | 18 | 15 | 9 | 12 | 9 | 108 | 85 | 442 |
| | F | 40 | 65 | 6 | 3 | 20 | 10 | 13 | 2 | 1 | 39 | 60 | 259 |
| UICC Classification | I | | 6 | | | | 3 | | 7 | 2 | 89 | 39 | |
| | II | | 33 | | | | 7 | | 3 | 4 | 20 | 37 | |
| | III | | 41 | | | | 6 | | 3 | 4 | 20 | 52 | |
| | IV | | 78 | | | | 9 | | 1 | 0 | 18 | 17 | |
| | unknown | | 2 | | | | 0 | | 0 | 0 | 0 | 0 | |

Results are shown in FIGS. 4 to 7.

The reproducibility of the competitive ELISA method was high (CV (coefficient of variance) median value: 0.079). The concentration of 565HP-α-fibrinogen according to the ELISA analysis was 2.26±2.28 (average value±standard deviation) in the case of plasmas from patients with pancreatic cancer of 160 cases, and 0.91±1.24 in the case of those from healthy subjects of 113 cases. There was significant difference between these cases in U test (p=3.80e-15). AUC of ROC curve between the patients with pancreatic cancer and the healthy subjects was 0.779.

Figure 4:
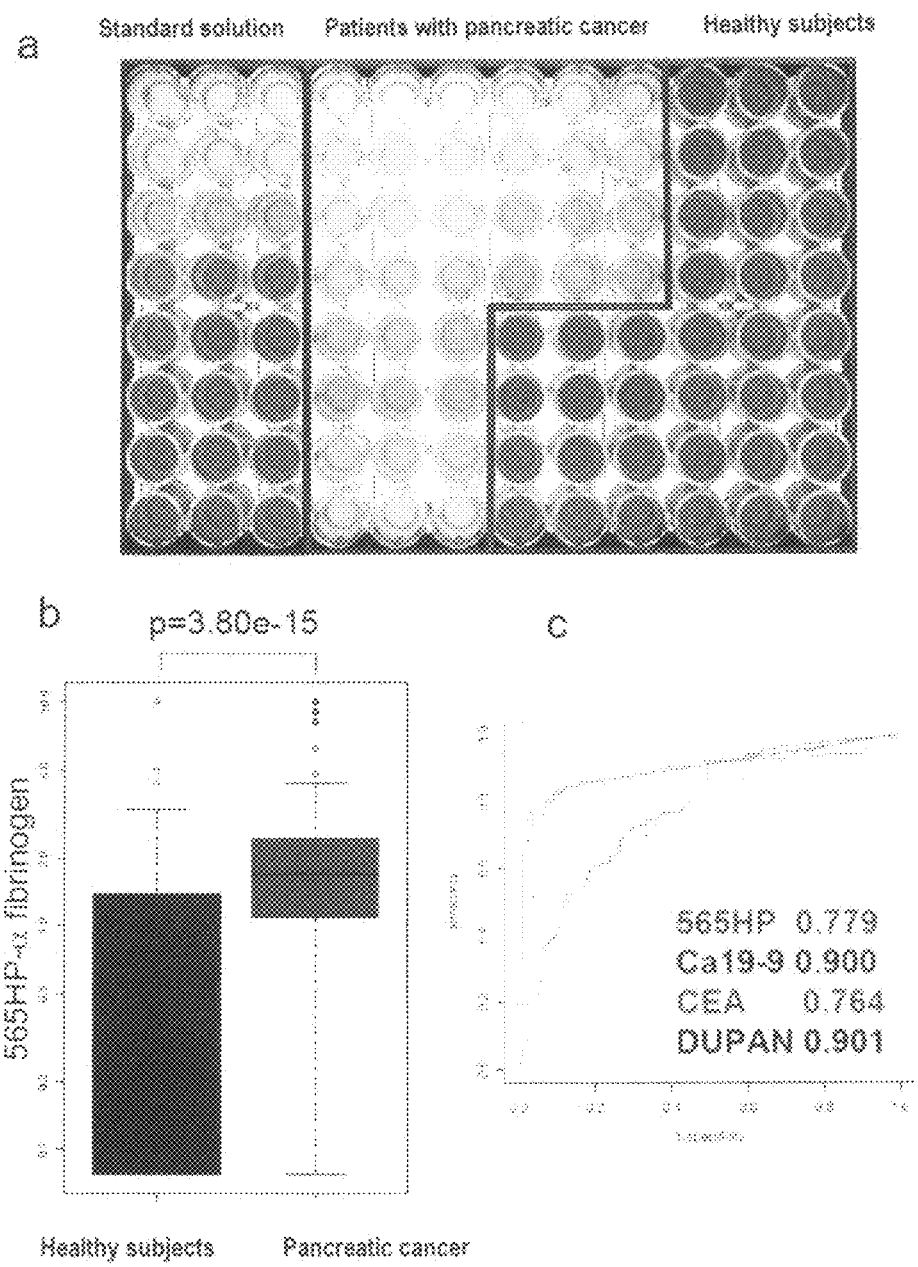
FIG. 4 shows results of analysis of expression of 565HP-α-fibrinogen in many clinical analytes using the ELISA method.

FIG. 4 shows results of analysis of expression of 565HP-α-fibrinogen in many clinical analytes using the ELISA method.
(a) Using the first to third lanes from the left of an ELISA plate, prepared standard samples (10, 5, 2.5, 1.25, 0.63, 0.31, 0.16, and 0.08 μg/ml) were measured. Data of the measurement of 12 patients with pancreatic cancer and 12 healthy subjects (3 times each) are shown (3 wells in the lateral direction show results of the measurement of one case 3 times).
(b) Expression of 565HP-α-fibrinogen in plasmas from patients with pancreatic cancer of 160 cases and healthy subjects of 113 cases is shown. The average value±standard deviation of the patients with pancreatic cancer was 2.26±2.28, whereas that of the healthy subjects was 0.91±1.24.
(c) ROC curve between the patients with pancreatic cancer and healthy subjects is shown. AUCs were as follows: 565HP-α-fibrinogen: 0.779, Ca19-9: 0.900, CEA: 0.764, and DUPAN: 0.901.

Figure 5:
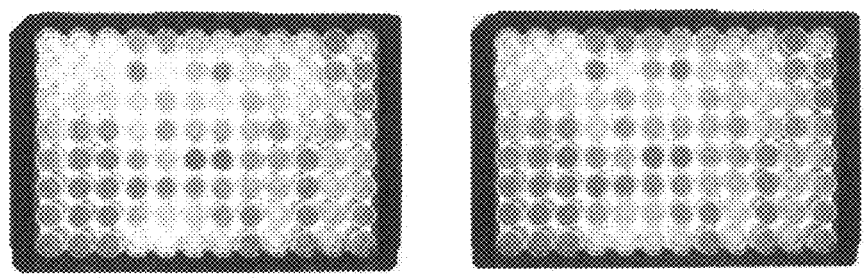
FIG. 5 shows results of analysis of expression of 565HP-α-fibrinogen in many clinical analytes using the ELISA method.
Figure 5:
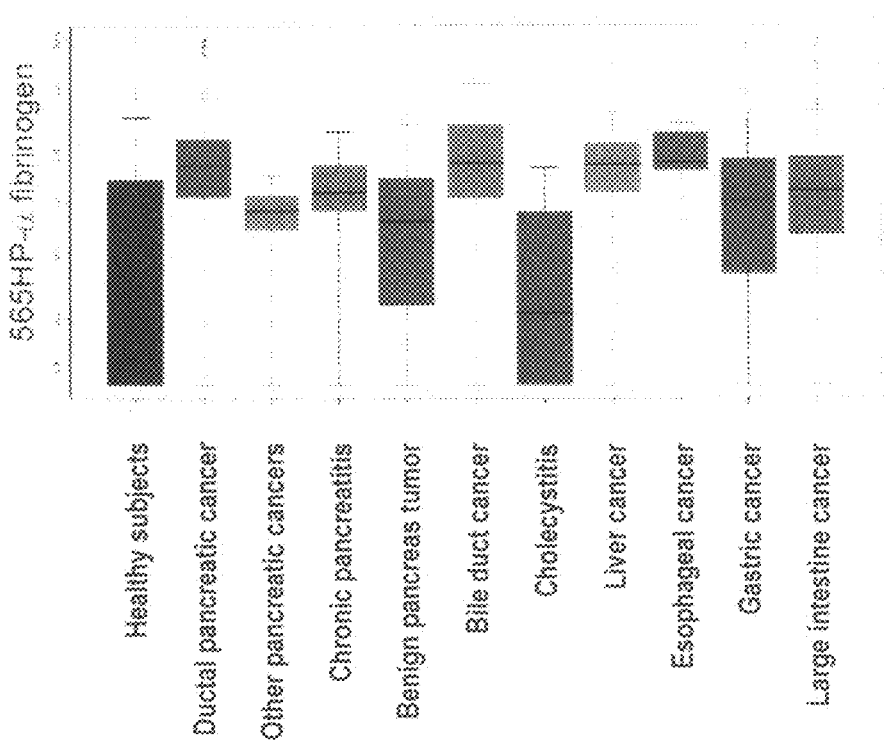

FIG. 5 shows results of analysis of expression of 565HP-α-fibrinogen in many clinical analytes using the ELISA method.
(a) Results of automatic ELISA measurement using Biomek FX are shown. One analyte is distributed to 3 plates (equal in quantity), and they were treated using the method according to the manual. Standard samples were put on each of the plates as described above, and using the standard curve utilizing the average values of the standard samples, the concentration on the plate was measured one by one.
(b) Results of the measurement of expression of 565HP-α-fibrinogen in clinical analytes shown in Table 1 are shown.

Figure 6:
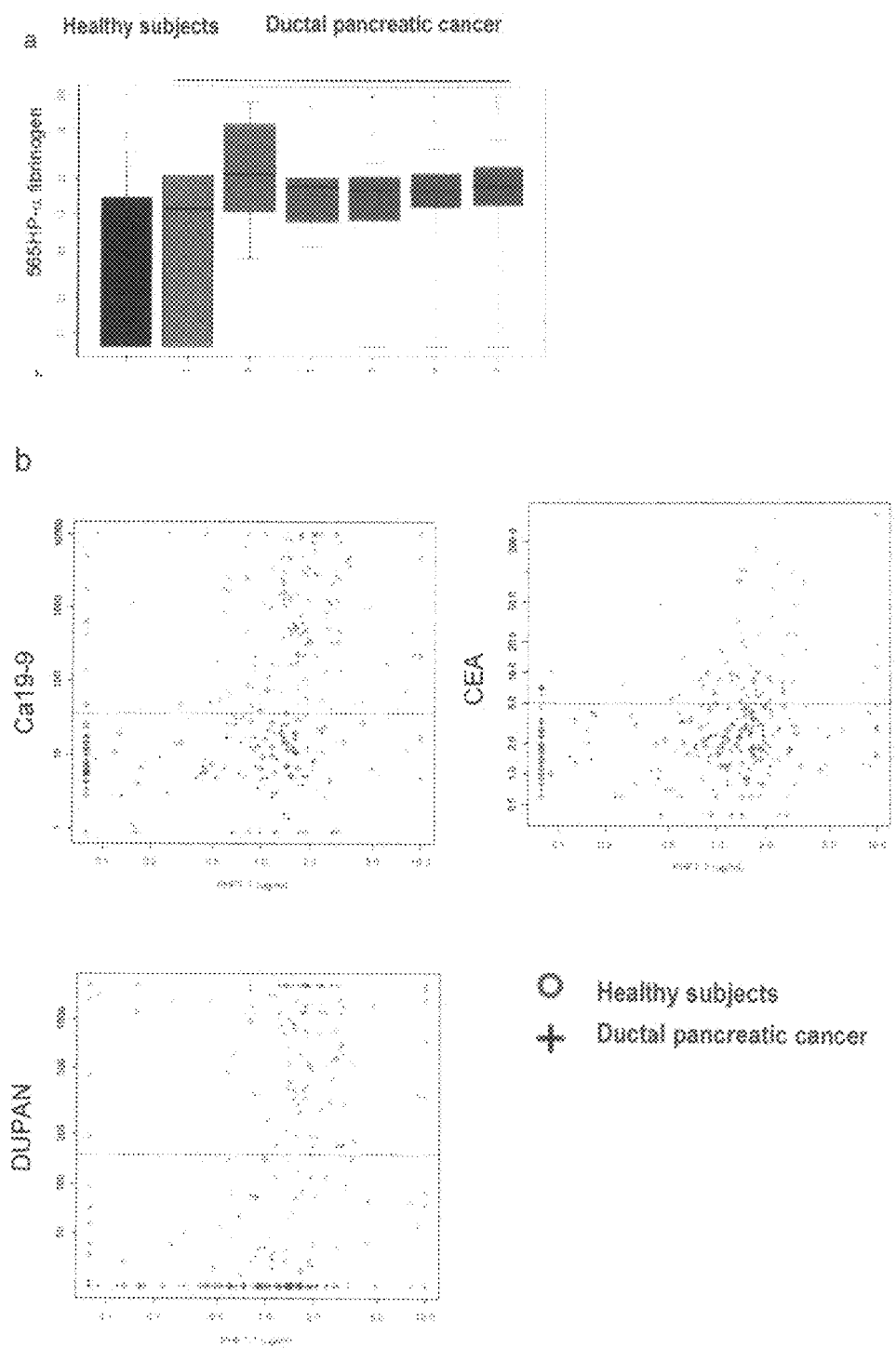
FIG. 6 shows analysis results of expression of 565HP-α-fibrinogen in patients with pancreatic cancer.

FIG. 6 shows analysis results of expression of 565HP-α-fibrinogen in patients with pancreatic cancer.
(a) Expression of 565HP-α-fibrinogen in patients with pancreatic cancer at respective UICC disease stages is shown.
(b) The relationship between existing tumor markers (Ca19-9, CEA and DUPAN) and expression of 565HP-α-fibrinogen is shown.

Figure 7:
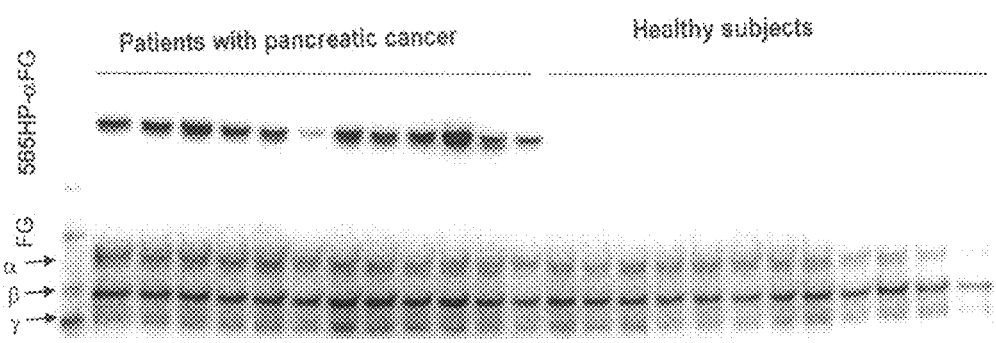
FIG. 7 shows the relation between 565HP-α-fibrinogen and α-fibrinogen.
Figure 7:
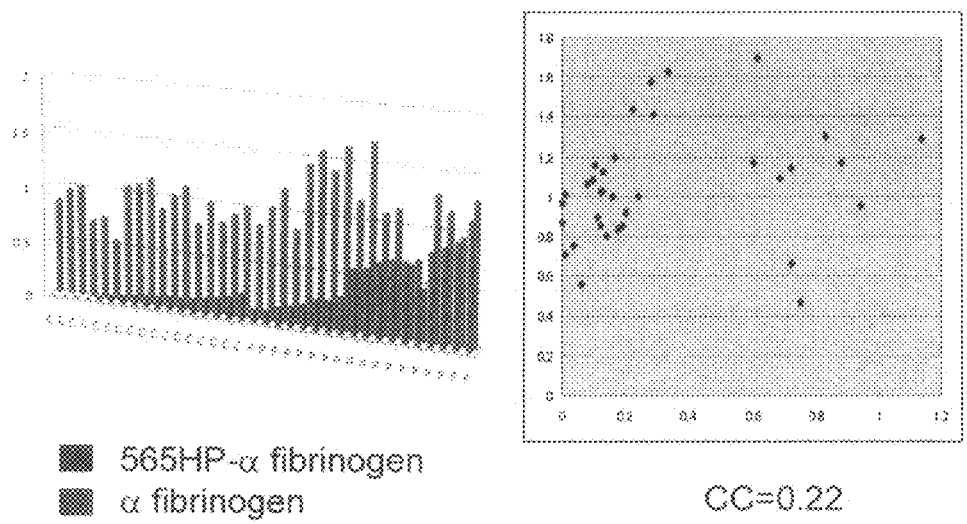

FIG. 7 shows the relation between 565HP-α-fibrinogen and α-fibrinogen.
(a) There was clear difference between 565HP-α-fibrinogen of the patients with pancreatic cancer and that of the healthy subjects. However, regarding α-fibrinogen, which is blotted by the existing antibody A0080 (DAKO, Glostrup, Denmark), there was no difference between them. Note that this antibody also stains β- and γ-fibrinogens.
(b) There was no correlation between expression of 565HP-α-fibrinogen and that of α-fibrinogen.

All publications cited herein are incorporated by reference herein in their entirety. It will be apparent to those skilled in the art that the present invention is described with reference to certain preferable embodiments, however, various modifications and variations can be made in the invention and specific examples provided herein without departing from the spirit or scope of the invention. Thus, it is intended that the invention covers the modifications and variations of this invention that come within the scope of any claims and their equivalents.

What is claimed is:

1. An isolated antibody that specifically binds to hydroxylated fibrinogen comprising at least one hydroxylated proline, wherein the isolated antibody has a higher affinity for the hydroxylated fibrinogen than for fibrinogen having no hydroxylated prolines, wherein when the hydroxylated fibrinogen is attached to a solid-phase in a reaction system for a competitive reaction between hydroxylated fibrinogen not attached to the solid-phase (antigen 1) and fibrinogen having no hydroxylated prolines (antigen 2), the antibody satisfies measurement conditions in which 50% inhibition activity of an antibody bound by the antigen 1 is at least 10-fold when compared to 50% inhibition activity of an antibody bound by the antigen 2, and wherein the hydroxylated fibrinogen attached to the solid-phase and the antigen 1 are represented by the amino acid sequence TFP(OH)GFFSPMLGEFVSETESR (SEQ ID NO: 3) or ESSSHEIP(OH)GIAEFPSR (SEQ ID NO: 4) (P(OH) represents hydroxylated proline), and wherein the amino acid sequence of the antigen 2 is represented by TFPGFFSPMLGEFVSETESR (SEQ ID NO: 1) or ESSSHHPGIAEFPSR (SEQ ID NO: 2).

2. The isolated antibody according to claim 1, wherein the antibody is a monoclonal antibody.

3. A detection reagent for a protein or polypeptide comprising an amino acid sequence in which a part of prolines in the molecule thereof are hydroxylated, the reagent comprising the isolated antibody according to claim 1.

4. The reagent according to claim 3, wherein the protein is fibrinogen.

5. The reagent according to claim 3, wherein the protein or polypeptide comprising an amino acid sequence in which a part of prolines in the molecule thereof are hydroxylated comprises an amino acid sequence in which a part of prolines in the amino acid sequence of (a) or (b) below are hydroxylated:

(a)   TFPGFFSPMLGEFVSETESR    (SEQ ID NO: 1)

(b)   ESSSHHPGIAEFPSR.        (SEQ ID NO: 2)

6. The reagent according to claim 3, wherein the protein or polypeptide comprising an amino acid sequence in which a part of prolines in the molecule thereof are hydroxylated comprises the amino acid sequence of (c) or (d) below:

(c)   TFP(OH)GFFSPMLGEFVSETESR    (SEQ ID NO: 3)

(d)   ESSSHHP(OH)GIAEFPSR         (SEQ ID NO: 4)

(P(OH) represents hydroxylated proline).

7. A detection or diagnostic agent for cancer, comprising the isolated antibody according to claim 1 or a reagent for a protein or polypeptide comprising an amino acid sequence in which a part of prolines in the molecule thereof are hydroxylated, the reagent comprising the isolated antibody according to claim 1.

8. The detection or diagnostic agent according to claim 7, wherein the cancer is pancreatic cancer.

9. A monoclonal antibody to hydroxylated fibrinogen comprising at least one hydroxylated praline, wherein the antibody has a higher affinity for the hydroxylated fibrinogen than for fibrinogen having no hydroxylated prolines, which is produced by a hybridoma whose accession number is FERM BP-11163.

10. The monoclonal antibody according to claim 9, wherein the hydroxylated fibrinogen is represented by TFP(OH)GFFSPMLGEFVSETESR (SEQ ID NO: 3) or ESSSHHP(OH)GIAEFPSR (SEQ ID NO: 4) (P(OH) represents hydroxylated proline).

11. A detection or diagnostic agent for cancer, comprising the isolated antibody according to claim 9 or a reagent for a protein or polypeptide comprising an amino acid sequence in which a part of prolines in the molecule thereof are hydroxylated, the reagent comprising the antibody according to claim 9.

12. The monoclonal antibody according to claim 9, wherein, in order to inhibit an immune reaction between the monoclonal antibody and the hydroxylated fibrinogen, wherein hydroxylated fibrinogen is attached to a solid-phase in a reaction system for a competitive reaction between hydroxylated fibrinogen not attached to the solid-phase (antigen 1) and fibrinogen having no hydroxylated prolines (antigen 2), the monoclonal antibody satisfies measurement conditions in which 50% inhibition activity to the immune reaction caused by the antigen 1 is at least 10-fold when compared to 50% inhibition activity to the immune reaction caused by the antigen 2.

13. The monoclonal antibody according to claim 12, wherein the amino acid sequence of the antigen 2 is represented by TFPGFFSPMLGEFVSETESR (SEQ ID NO: 1) or ESSSHHPGIAEFPSR (SEQ ID NO: 2).

14. The monoclonal antibody according to claim 12, wherein the hydroxylated fibrinogen attached to the solid-phase and the antigen 1 comprise the amino acid sequence TFP(OH)GFFSPMLGEFVSETESR (SEQ ID NO: 3) or ESSSHHEP(OH)GIAEFPSR (SEQ ID NO: 4) (P(OH) represents hydroxylated proline).

15. A detection reagent for a protein or polypeptide comprising an amino acid sequence in which a part of prolines in the molecule thereof are hydroxylated, the reagent comprising the monoclonal antibody according to claim 9.

16. The reagent according to claim 15, wherein the protein is fibrinogen.

17. The reagent according to claim 15, wherein the protein or polypeptide comprising an amino acid sequence in which a part of prolines in the molecule thereof are hydroxylated comprises the amino acid sequence of (c) or (d) below:

```
(c)   TFP(OH)GFFSPMLGEFVSETESR   (SEQ ID NO: 3)

(d)   ESSSHHP(OH)GIAEFPSR        (SEQ ID NO: 4)

(P(OH) represents hydroxylated proline).
```

18. An isolated hybridoma cell which produces the monoclonal antibody according to claim 9.

19. An isolated antibody that specifically binds to hydroxylated fibrinogen comprising at least one hydroxylated proline, wherein the isolated antibody has a higher affinity for the hydroxylated fibrinogen than for fibrinogen having no hydroxylated prolines,
wherein when the hydroxylated fibrinogen is attached to a solid-phase in a reaction system for a competitive reaction between hydroxylated fibrinogen not attached to the solid-phase (antigen 1) and fibrinogen having no hydroxylated prolines (antigen 2), the antibody satisfies measurement conditions in which 50% inhibition activity of an antibody bound by the antigen 1 is at least 10-fold when compared to 50% inhibition activity of an antibody bound by the antigen 2, and wherein the hydroxylated fibrinogen attached to the solid-phase and the antigen 1 are represented by the amino acid sequence TFP(OH)GFFSPMLGEFVSETESR (SEQ ID NO: 3) or ESSSHHP(OH)GIAEFPSR (SEQ ID NO: 4) (P(OH) represents hydroxylated proline), and wherein the amino acid sequence of the antigen 2 is represented by TFPGFFSPMLGEFVSETESR (SEQ ID NO: 1) or ESSSHHPGIAEFPSR (SEQ ID NO: 2), and
wherein the isolated antibody specifically binds to a site to which a monoclonal antibody which is produced by the hybridoma whose accession number is PERM BP-11163 specifically binds.

20. An isolated hybridoma cell which produces an antibody to hydroxylated fibrinogen comprising at least one hydroxylated proline, wherein the antibody has a higher affinity for the hydroxylated fibrinogen than for fibrinogen having no hydroxylated prolines, wherein the accession number of the cell line is FERM BP-11163.

21. A monoclonal antibody or an antigen binding fragment thereof produced by hybridoma having accession number PERM BP-11163.

22. A monoclonal antibody or an antigen binding fragment thereof which binds to the same epitope as the monoclonal antibody produced by hybridoma having accession number FERM BP-11163.

* * * * *